US005654446A

United States Patent [19]
Ognyanov et al.

[11] Patent Number: 5,654,446
[45] Date of Patent: Aug. 5, 1997

[54] PROCESS FOR THE PREPARATION OF DIHYDROARTEMISININ HEMISUCCINATE

[75] Inventors: Iliya Vassilev Ognyanov; Angel Nikolov Konakchiev, both of Sofia, Bulgaria; Ralph Hänni, Füllinsdorf, Switzerland

[73] Assignee: Mepha AG, Aesch, Switzerland

[21] Appl. No.: 624,744

[22] Filed: Mar. 27, 1996

[30] Foreign Application Priority Data

Apr. 3, 1995 [BG] Bulgaria ................................. 99545

[51] Int. Cl.$^6$ ............................................... C07D 321/00
[52] U.S. Cl. ................................................................ 549/348
[58] Field of Search .............................................. 549/348

[56] References Cited

PUBLICATIONS

Chemical Abstracts, vol. 98, No. 1, 3 Jan. 1983, abstract No. 4420h, Li et al.
D. Shaofeng et al., "$^3$H Labeling of QHS Derivatives", *Bull Chin. Materia Medica*, 6 (4), 25–27 (1981).
Y. Li et al., "Synthesis of Ethers, Carboxylic Esters and Carbonates of Dihydroarthemisinin", Acta Pharm. Sin., 16 (6), 429–439 (1981).
H.J. Woerdenbag et al., "Artemisia annua L.: a source of novel antimalarial drugs", *Pharm. Weekblad Sci.*, 12 (5), 169–181 (1990).
A. Brossi et al., "Arteether, a New Antimalarial Drug: Synthesis and Antimalarial Properties", *J. Med. Chem.*, 31, 645–650 (1988).
H. J. Woerdenbag et al., "Progress in the research of artemis–inin–related antimalarials: an update", *Pharm. World Sci.*, 16, (4), 169–180 (1994).
T. T. Hien et al., "Qinghaosu", *The Lancet*, 341, 603–608 (1993).
S.S. Zaman et al., "Some Aspects of the Chemistry and Biological Activity of Artemisinin and Related Antimalarials", *Heterocycles* 32 (8), 1593–1638 (1991).
A. R. Butler et al., Artemisinin (Qinghaosu) : "A New Type of Antimalarial Drug", *Chem. Soc. Reviews*, 85–90 (1992).
D. L. Klayman, Qinghaosu (Artenisinin) : "An Antimalarial Drug from China", *Science* 228, 1049–1055 (1985).
ACTA Chimica Sinica, vol. 40, No. 6, Jun., 1982.
Chemical Abstracts, vol. 119, No. 23, 6 Dec. 1993, abstract No. 249761a, Chau et al.
Lin et al., Chemical Abstracts, vol. 107, No. 19, 9 Nov. 1987, abstract No. 168241f.
Lin et al., J. Med. Chem., "Antimalarial activity of new water–soluble dihydroartemisinin derivatives", pp. 2147–2150. vol. 30 No. 11 (1987).

*Primary Examiner*—Amelia Owens
*Attorney, Agent, or Firm*—Leydig, Voit & Mayer

[57] ABSTRACT

Dihydroartemisinin hemisuccinate is prepared by acylation of dihydroartemisinin with 1.0 to 1.3 molar equivalents of succinic anhydride in the presence of 0.5 to 1.5 molar equivalents of tri($C_1$–$C_3$-alkyl)amine in a low-boiling, neutral, water-miscible, inert organic solvent or solvent mixture and subsequent isolation of the product at pH 5–8. The product is obtained directly in crystalline form and high yield.

9 Claims, No Drawings

PROCESS FOR THE PREPARATION OF DIHYDROARTEMISININ HEMISUCCINATE

FIELD OF THE INVENTION

The present invention relates to an improved process for the preparation of dihydroartemisinin hemisuccinate, with the chemical name [3R-(3α,5aβ,6β,8aβ,9α,10β,12β,12aR*)]-butanedioic acid mono(decahydro-3,6,9-trimethyl-3,12-epoxy-12H-pyrano[4,3-j]-1,2-benzodioxepin-10-yl)ester, by acylation of [3R-(3α,5aβ,6β,8aβ,9α,10,12β,12aR*)]-decahydro-10-hydroxy-3,6,9-trimethyl-3,12-epoxy-12H-pyrano[4,3-j]-1,2-benzodioxepin. Mixtures of the 10α-hydroxy and 10β-hydroxy epimers of the latter are also known under the names dihydroartemisinin and dihydroqinghaosu. For the hemisuccinate and its sodium salt the designation artesunate is also customary (and for the hemisuccinate the English designation artesunic acid).

BACKGROUND OF THE INVENTION

The sesquiterpene endoperoxide lactone artemisinin and its 10α derivative dihydroartemisinin hemisuccinate are used in chemotherapy against ordinary and severe (acute) infections with Plasmodium falciparum, which is responsible for 85% of malarial illnesses. The chemistry and the antiprotozoal action of these compounds is described in the following publications: H. J. Woerdenbag et al., Progress in the Research of Artemisinin-related Antimalarials: An Update, Pharm. World Sci. 16 (4), 169–180 (1994); T. T. Hien et al., Qinghaosu, The Lancet 341, 603–608 (1993); A. R. Butler et al., Artemisinin (Qinghaosu): A New Type of Antimalarial Drug, Chem. Soc. Reviews 85–90 (1992); S. S. Zaman et al., Some Aspects of the Chemistry and Biological Activity of Artemisinin and Related Antimalarials, Heterocycles 32 (8), 1593–1638 (1991); H. J. Woerdenbag et al., Artemisia annua L.: a Source of Novel Antimalarial Drugs, Pharm. Weekblad Sci. 12 (5), 169–181 (1990); D. L. Klayman, Qinghaosu (Artemisinin): An Antimalarial Drug from China, Science 228, 1049–1055 (1985).

The water-insoluble dihydroartemisinin hemisuccinate is customarily administered orally in the form of tablets or rectally in the form of suppositories, while the water-soluble sodium salt (sodium artesunate) is administered intravenously.

Dihydroartemisinin hemisuccinate, together with a number of other 10-ester and 10-ether derivatives of dihydroartemisinin, was synthetically prepared for the first time by Chinese scientists at the end of 1979 to the beginning of 1980. D. Shaofeng et al., ³H Labeling of QHS Derivatives, Bull. Chin. Materia Medica 6 (4), 25–27 (1981) and Y. Li et al., Synthesis of Ethers, Carboxylic Esters and Carbonates of Dihydroartemisinin, Acta Pharm. Sin. 16 (6), 429–439 (1981) describe the preparation of dihydroartemisinin hemisuccinate by acylation of dihydroartemisinin with succinic anhydride in pyridine. In the last-mentioned publication, in which this process was presented as general method $A_1$ for the preparation of various dihydroartemisinin 10-esters, it was possible to obtain the dihydroartemisinin hemisuccinate in a yield of 60% by means of warming dihydroartemisinin and succinic anhydride in pyridine at 30° C. for 24 hours.

An improved version of the acylation of dihydroartemisinin, designated as method $B_1$, was proposed by L. Ying et al. in The Synthesis of Some Carboxylic Esters and Carbonates of Dihydroartemisinin by Using 4-(N,N-Dimethylamino)pyridine as an Active Acylation Catalyst, Acta Chim. Sinica 40 (6), 557–561 (1982) and described in detail with the aid of the preparation of dihydroartemisinin-10-valerate. In this process, 2 mmol of dihydroartemisinin were dissolved in 30 ml of 1,2-dichloroethane and treated with 4 mmol of valetic anhydride, 0.33 mmol of 4-(N,N-dimethylamino)pyridine and 29 mmol of triethylamine, and the mixture was stirred at room temperature until dihydroartemisinin had been used up. The reaction mixture was then acidified with dilute hydrochloric acid and the aqueous phase was separated off. The oily residue, obtained after washing and drying the organic phase and distilling off the solvent, was purified by chromatography on silica gel using petroleum ether 60°–90°/ethyl acetate 10:1 as eluent.

The use of this procedure for the preparation of the dihydroartemisinin hemisuccinate, but with dihydroartemisinin, succinic anhydride and 4-(N,N-dimethylamino)pyridine in the molar ratio 1:1.5:0.20 and a reaction time of 5 hours, afforded dihydroartemisinin hemisuccinate in a yield of 65%.

The known methods $A_1$ and $B_1$ for the acylation of dihydroartemisinin require the presence of organic bases, namely the presence of pyridine in method $A_1$, and the presence of triethylamine and 4-(N,N-dimethylamino)pyridine in method $B_1$. The use of organic bases in the acylation of alcohols with acyl halides or acyl anhydrides is customary practice, and it is known that organic bases can serve not only as catalysts, but also for the neutralization of the acid liberated during the acylation (cf. F. A. Carey and R. J. Sundberg, Advanced Organic Chemistry, Third Edition, Part A, page 476, Plenum Press, New York, 1991).

Until now, only these two Chinese methods $A_1$ and $B_1$ for the synthesis of the dihydroartemisinin hemisuccinate have been made public, which, however, are unsuitable for the preparation of larger amounts and not only are not very economical, but also would involve considerable technical and/or environmental problems with respect to the working up and disposal of the solvents, reagents and by-products. In particular, chromatographic separation is not practicable in the production of larger amounts. Furthermore, in the improved version $B_1$ the use of pyridine as a solvent is in fact avoided, but 4-(N,N-dimethylamino)pyridine is employed as a catalyst and, as a solvent, 1,2-dichloroethane is used, which is ecologically not entirely acceptable and after distillation partly remains behind as contamination of the product. Moreover, comparatively large amounts of solvent and reagents are needed in the previously known process $B_1$, namely 15 l of 1,2-dichloroethane and 14 mole of triethylamine per mole of dihydroartemisinin and furthermore a 50–100% excess of succinic anhydride.

DESCRIPTION OF THE INVENTION

The object of the present invention is the development of an improved process which avoids the disadvantages of the previously known processes and which, in particular, is also suitable for the preparation of larger amounts of dihydroartemisinin hemisuccinate.

The object is achieved according to the invention using a process for the preparation of the 10α epimer of dihydroartemisinin hemisuccinate of the formula

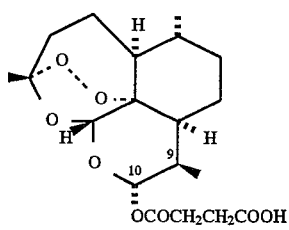

OCOCH₂CH₂COOH by acylation of dihydroartemisinin of the formula II

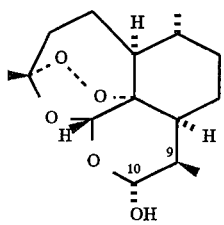

OH with succinic anhydride, which is characterized in that the acylation is carried out with 1.0 to 1.3 molar equivalents of succinic anhydride in the presence of 0.5 to 1.5 molar equivalents of tri($C_1$–$C_3$-alkyl)amine, relative to dihydroartemisinin, in a low-boiling, neutral, water-miscible, inert organic solvent or solvent mixture and the hemisuccinate is then isolated at pH 5 to 8.

The process according to the invention avoids the use of pyridine or 1,2-dichloroethane, and at the same time it allows 4-(N,N-dimethyl-amino)pyridine to be dispensed with completely as a catalyst. Surprisingly, it was furthermore found that the amounts of solvents and reagents can be clearly decreased and nevertheless a significant improvement in the yield to values of about 93% and higher results. In addition, the acylation reaction according to the invention proceeds substantially more rapidly than the previously known processes, and the product can be obtained directly in crystalline form in a purity of over 98%, whereby chromatographic separation processes are unnecessary. The process according to the invention is thus especially suitable for the preparation of dihydroartemisinin hemisuccinate, even on the industrial scale, and compared with the previously known processes it has significant advantages from an economic and ecological point of view.

The process according to the invention yields only the 10α epimer of the dihydroartemisinin hemisuccinate, independently of the configuration on the $C_{10}$ atom of the starting material of the formula II. The 10α-hydroxy epimer, the 10β-hydroxy epimer or a mixture of these epimers can therefore be used as the starting material in the process according to the invention.

The acylation of dihydroartemisinin can in principle be carried out with an equimolar amount of succinic anhydride, if water is completely excluded. In general, however, the use of a small excess is to be recommended.

In principle, all tri($C_1$–$C_3$-alkyl)amines, such as trimethylamine, methyldiethylamine, triethylamine and tripropylamine, or their mixtures, are suitable bases. In general, triethylamine is preferred. The tri($C_1$–$C_3$-alkyl)amine is expediently used in an amount of at least 0.5 molar equivalents, relative to dihydroartemisinin, in order to guarantee adequate buffering of the reaction medium. An amount of 0.7 to 1.2 molar equivalents, for example 0.8 molar equivalents, is preferred.

The acylation is carried out according to the invention in a low-boiling, neutral, water-miscible, inert organic solvent or a mixture of such solvents. The expressions "low-boiling" and "neutral" relate, in the context of the present invention, to those solvents which have a low boiling point of preferably at most about 120° C. and no acidic or basic groups (such as carboxyl groups, amino groups etc.). Preferably, however, the boiling point of the solvent is at least about 50° C. if the acylation is not carried out in a closed reactor under pressure. Open-chain or cyclic ketones and ethers, such as acetone, methyl ethyl ketone, tetrahydrofuran, dioxane and the like, are in general preferred. Acetone, tetrahydrofuran, dioxane and mixtures of these solvents are particularly preferred. In general, about 3–5 l of solvent per 1 kg of dihydroartemisinin are completely adequate for carrying out the acylation. The amount of solvent, however, is not critical, and higher amounts in particular can also be used.

The temperature and pressure of the acylation reaction are not critical. In general, however, a temperature of 20° to 60° C. is preferred. In particular, the reaction can also be carried out at atmospheric pressure and room temperature. The reaction time under these conditions is typically about 0.5 hours. However, monitoring the course of the reaction is to be recommended, for example by means of thin-layer chromatography.

After acylation is complete, a pH of 5–8 is set by means of acid and the desired dihydroartemisinin hemisuccinate is isolated. In this connection, addition first of water and then of acid is advantageous in order to precipitate the product in crystalline form and in order to facilitate separation of the product by filtration. Preferably, about 3–12 l of water are used per 1 kg of dihydroartemisinin. Organic and inorganic acids, such as acetic acid, hydrochloric acid, sulphuric acid and the like are suitable for the neutralization; dilute hydrochloric acid is preferred. Preferably, a pH of 5.5–7.5, in particular about 6.5, is set. The temperature is not critical and can be, for example, 20° to 70° C. In particular, working up can also be carried out at room temperature or lower temperature.

The drying of the hemisuccinate obtained is preferably carried out at a temperature of at most 60° C.

The dihydroartemisinin used as a starting material can be prepared in a known manner by reduction of artemisinin with sodium borohydride; cf. A. Brossi et al., Arteether, a New Antimalarial Drug: Synthesis and Antimalarial Properties, J. Med. Chem. 31, 645–650 (1988).

The process according to the invention is illustrated further by the following examples. As starting material, a mixture of the 10α and the 10β epimer of dihydroartemisinin in the approximate ratio of 40:60 was in each case used, which contained less than 1% of unreduced artemisinin. The reagents and solvents corresponded to the "pure" Merck grade. The purity of the dihydroartemisinin 10α-hemisuccinate obtained was checked by means of thin-layer chromatography, melting point measurement and HPLC, and its identity was confirmed by comparison with an authentic sample by means of $^1$H-NMR and IR spectra, thin-layer chromatography and HPLC.

EXAMPLE 1

0.45 g (4.5 mmol) of succinic anhydride was dissolved at 25° C. in a mixture of 3 ml of dry acetone and 0.4 ml (0.29 g; 2.9 mmol) of triethylamine. 1.0 g (3.52 mmol) of dihydroartemisinin was added to the solution and the mixture was stirred until the dihydroartemisinin had reacted completely (checking by means of thin-layer chromatography). 12 ml of water were then added to the reaction mixture with stirring, and the semicrystalline, milky suspension was adjusted to pH 6.5 with dilute hydrochloric acid. The solid, crystalline precipitate obtained was filtered off and washed with distilled water until the filtrate was neutral and free of chloride ions. After drying, 1.28 g (95.0%) of, according to thin-layer chromatography, pure dihydroartemisinin hemisuccinate of m.p. 140°–142° C. were obtained.

EXAMPLE 2

With 1.0 g dihydroartemisinin and carried out as described in Example 1, but using 4 ml of tetrahydrofuran instead of acetone, 1.30 g (96.5%) of dihydroartemisinin hemisuccinate of m.p. 139.5°–142° C. was obtained.

EXAMPLE 3

With 1.0 g dihydroartemisinin and carried out as described in Example 1, but using 4 ml of dioxane instead of acetone, 1.25 g (92.8%) of dihydroartemisinin hemisuccinate of m.p. 140.5°–142.5° C. was obtained.

EXAMPLE 4

With 1.0 g dihydroartemisinin and carried out as described in Example 1, but using 4 ml of a 1:1 mixture of acetone and tetrahydrofuran instead of acetone, 1.30 g (95.8%) of dihydroartemisinin hemisuccinate of m.p. 141°–143° C. was obtained.

EXAMPLES 5–8

Using higher amounts of dihydroartemisinin (DHA), succinic anhydride (SA), triethylamine [$N(C_2H_5)_3$] and acetone four further experiments were carried out by the same method and under identical conditions to those described in Example 1. The amounts used, the yields of dihydroartemisinin hemisuccinate obtained and the melting point of the product are given in Table 1.

TABLE 1

| Ex- | DHA | SA | N ($C_2H_5$)$_3$ | Acetone | Yield | | M.p. |
|---|---|---|---|---|---|---|---|
| ample | g | g | ml | ml | g | % | °C. |
| 5 | 50 | 23 | 20 | 150 | 61.5 | 91.8 | 140–142 |
| 6 | 100 | 45 | 40 | 300 | 124.7 | 92.2 | 141.5–143.5 |
| 7 | 300 | 135 | 120 | 900 | 394.0 | 97.2 | 140–142 |
| 8 | 400 | 180 | 160 | 1200 | 515.0 | 95.2 | 140.5–142.5 |

We claim:

1. Process for the preparation of the 10α epimer of dihydroartemisinin hemisuccinate of the formula

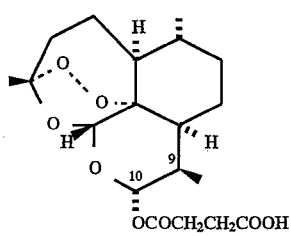

comprising acylation of dihydroartemisinin of the formula

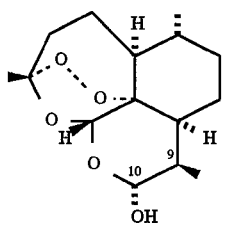

with succinic anhydride, wherein the acylation is carried out with 1.0 to 1.3 molar equivalents of succinic anhydride in the presence of 0.5 to 1.5 molar equivalents of tri($C_1$–$C_3$-alkyl)amine, relative to dihydroartemisinin, in a low-boiling, neutral, water-miscible, inert organic solvent or solvent mixture and the hemisuccinate is then isolated at pH 5 to 8.

2. Process according to claim 1, wherein tri($C_1$–$C_3$-alkyl)amine is used in an amount of 0.7 to 1.2 molar equivalents, relative to dihydroartemisinin.

3. Process according to claim 1, wherein the tri($C_1$–$C_3$-alkyl)amine used is triethylamine.

4. Process according to claim 1 wherein the organic solvent used is a ketone and/or an ether.

5. Process according to claim 1 wherein the organic solvent used is acetone, tetrahydrofuran and/or dioxane.

6. Process according to claim 1 wherein the organic solvent or solvent mixture is used in an amount of 3–5 l per 1 kg of dihydroartemisinin.

7. Process according to claim 1 wherein the acylation is carried out at 20° to 60° C.

8. Process according to claim 1 wherein water is added to the reaction mixture after acylation has taken place and a pH of 5 to 8 is set by addition of acid.

9. Process according to claim 8, wherein the acid used is dilute hydrochloric acid.

* * * * *